United States Patent [19]
Shefaram et al.

[11] Patent Number: 6,019,772
[45] Date of Patent: Feb. 1, 2000

[54] ATHERECTOMY DEVICE

[75] Inventors: Adi Shefaram, Hertzlia Pituah; Youval Katzman, Zichron Yaacov, both of Israel

[73] Assignee: Arteria Medical Sciences, Inc., San Francisco, Calif.

[21] Appl. No.: 09/158,038

[22] Filed: Sep. 21, 1998

[51] Int. Cl.[7] .................................................. A61B 17/32
[52] U.S. Cl. ......................................................... 606/159
[58] Field of Search .................................. 606/159, 180, 606/170, 176; 604/22

[56] References Cited

U.S. PATENT DOCUMENTS

| | | | |
|---|---|---|---|
| 4,020,847 | 5/1977 | Clark, III | 128/305 |
| 4,979,951 | 12/1990 | Simpson | 606/159 |
| 5,282,484 | 2/1994 | Reger | 606/159 |
| 5,366,464 | 11/1994 | Belknap | 606/159 |
| 5,584,843 | 12/1996 | Wulfman et al. | 606/159 |

Primary Examiner—Michael Buiz
Assistant Examiner—Kevin Truong
Attorney, Agent, or Firm—Fish & Neave; Nicola A. Pisano

[57] ABSTRACT

An atherectomy device is provided wherein a catheter has a cutting region including plurality of slotted tubular members interconnected by flexible segments. Each slotted tubular member includes cutting edges that sever occlusive material from the interior of a vessel when the cutting region is rotated. The flexible segments may be formed by cutting windows in a tapered hollow tubular member, or may comprise bellows-shaped tubes or helical coils, and may be coated with a flexible material allowing suction to be drawn through the device, or to permit the delivery of contrast agents, dyes, fluids or drugs to the operative site. A guide catheter also may be provided for positioning the cutting region of the atherectomy device at the operative site.

26 Claims, 2 Drawing Sheets

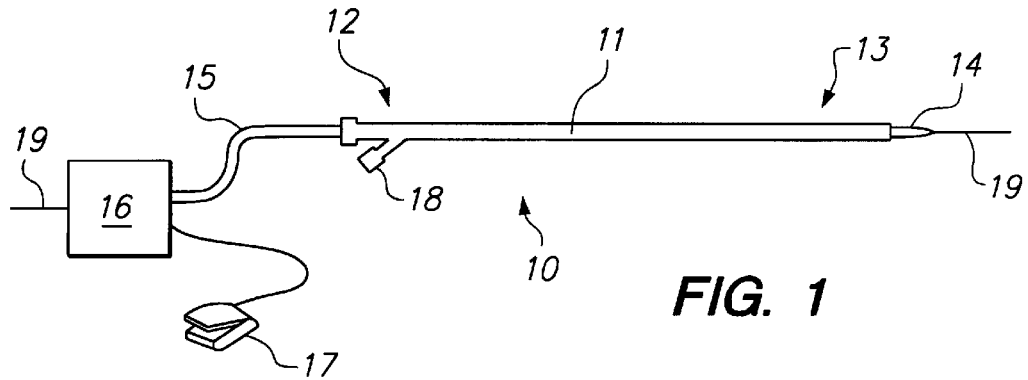
FIG. 1
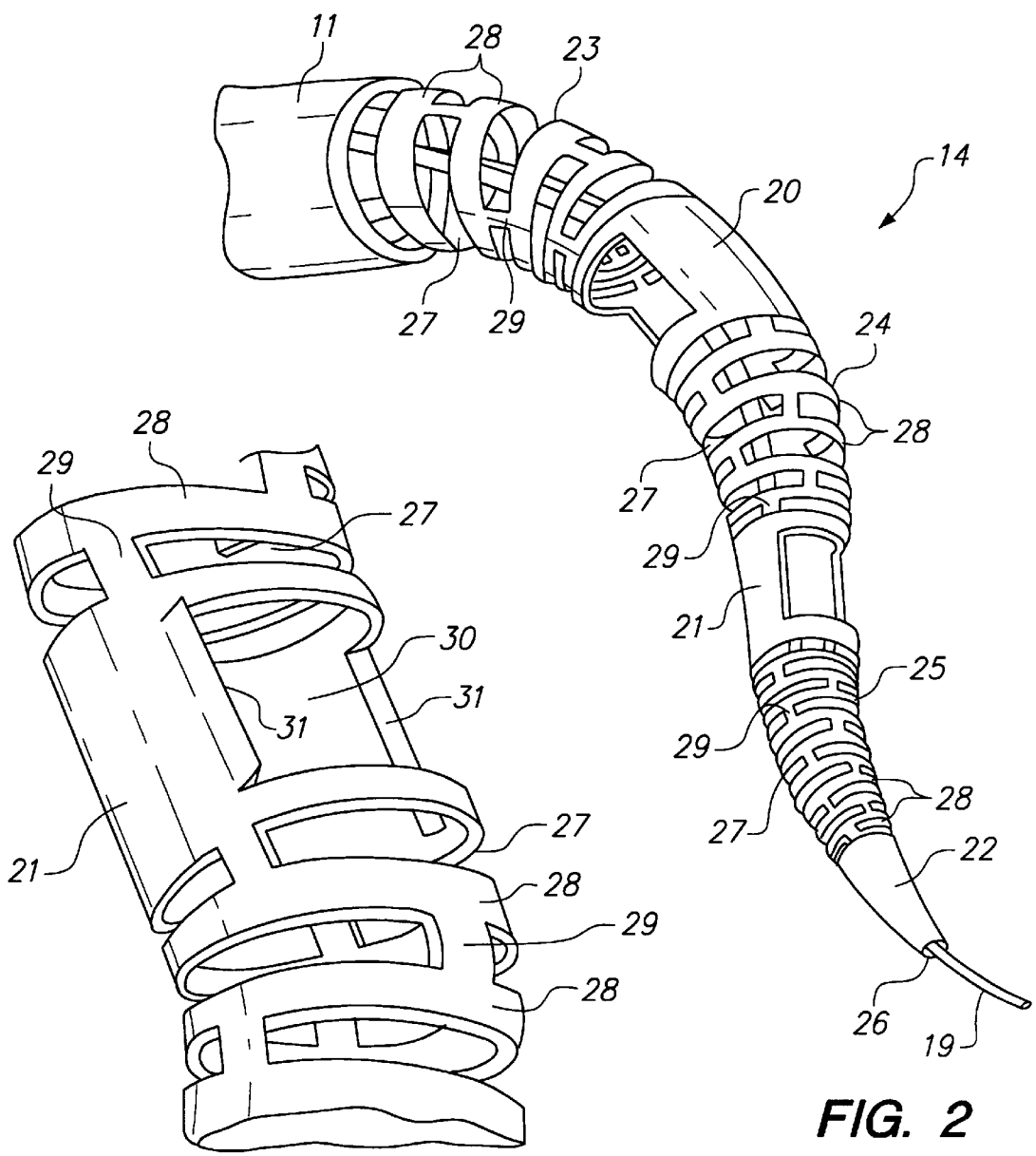
FIG. 2
FIG. 3

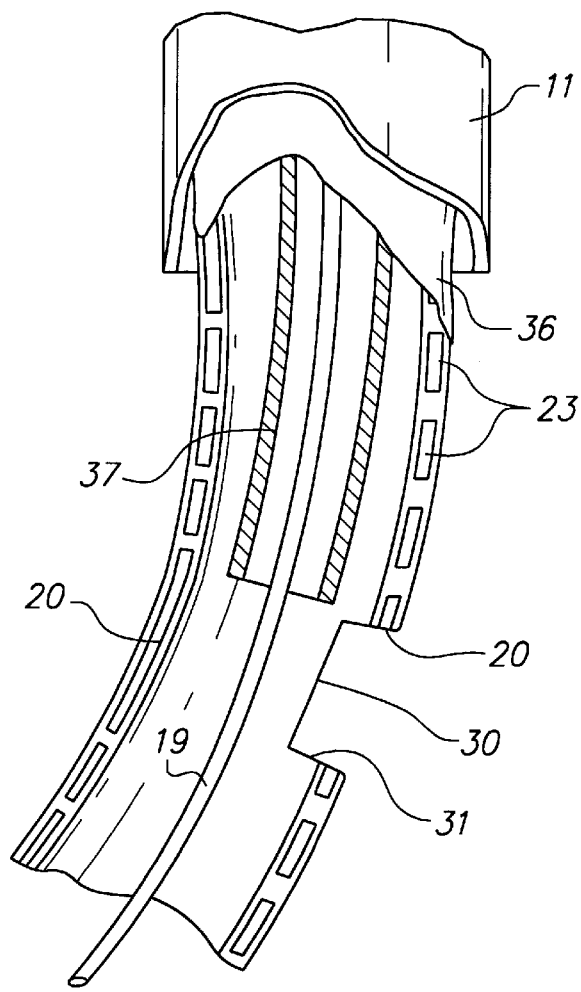
FIG. 4
FIG. 5

ATHERECTOMY DEVICE

FIELD OF THE INVENTION

The present invention relates to apparatus for providing removing occlusive material from the interior of a vessel or stent to restore bloodflow therethrough.

BACKGROUND OF THE INVENTION

A number of atherectomy devices have been developed to remove occlusive material, such as plaque and cellular overgrowths, from the interior of a vessel to restore blood flow through the vessel. While many of these previously known devices have been widely accepted for use in interventional procedures, such devices continue to have drawbacks that limit the applicability of the devices in certain circumstances.

U.S. Pat. No. 4,979,951 to Simpson describes a device wherein a distal region carries a housing having an elongated slot. A cutting member disposed within the housing reciprocates pass the slot to sever material protruding into the housing. A drawback of the Simpson device is that it is useful only in arteries large enough to accommodate the housing. In addition, that device cannot be used to remove occlusive material from the walls of tortuous vessels, because the device is incapable of conforming adequately to a curved vessel wall.

U.S. Pat. No. 5,366,464 to Belknap describes an atherectomy device formed from a tapered helical coil covered with a polymeric sheath. A plurality of elongated slots are formed in the helical coil so that the severed ends of adjacent turns of the coil form a flexible cutting edge. While the Belknap device offers the advantages of conforming to tortuous anatomy, and being able to access smaller vessels, it has been determined that the device is prone to failure during use. Specifically, the sheath material in the vicinity of the windows is incapable of sustaining the high torque loads imposed during operation of the device.

U.S. Pat. No. 4,020,847 to Clark describes a rotating cutter device including a slotted cylindrical member disposed at the end of a helical coil. The length of the slotted cylindrical member may make it difficult for the device to pass through or remove occlusive material in tortuous anatomy, or to insert the cutting device into smaller arteries.

In view of the foregoing, it would be desirable to provide an atherectomy device that permits occlusive material to be removed from tortuous and small diameter vessels, and which overcomes the disadvantages of previously known devices.

It further would be desirable to provide an atherectomy device capable of being configured to excise occlusive material from tapered arteries.

It still further would be desirable to provide an atherectomy device that enables occlusive material to be removed from vessels having a tortuous anatomy.

SUMMARY OF THE INVENTION

In view of the foregoing, it is an object of this invention to provide an atherectomy device that permits occlusive material to be removed from tortuous and small diameter vessels, and which overcomes the disadvantages of previously known devices.

It is another object of the present invention to provide an atherectomy device capable of being configured to excise occlusive material from tapered arteries.

It is a further object of this invention to provide an atherectomy device that enables occlusive material to be removed from vessels having a tortuous anatomy.

These and other objects of the present invention are accomplished by providing an atherectomy device comprising a catheter having a cutting region including plurality of slotted tubular members interconnected by flexible segments. Each slotted tubular member includes cutting edges that sever occlusive material from the interior of a vessel when the cutting region is rotated. The flexible segments may be formed by cutting windows in a tapered hollow tubular member, or may comprise bellows-shaped tubes or helical coils. The flexible segments may be coated with a flexible polymeric material to allow suction to be drawn through the device, or to permit the delivery of contrast agents, dyes, fluids or drugs to the operative site. A guide catheter may be used for positioning the cutting region of the atherectomy device at the operative site.

BRIEF DESCRIPTION OF THE DRAWINGS

Further features of the invention, its nature and various advantages will be more apparent from the accompanying drawings and the following detailed description of the preferred embodiments, in which:

FIG. 1 is a perspective view of an illustrative embodiment of an atherectomy device constructed in accordance with the principles of the present invention;

FIG. 2 is a detailed perspective view of the cutting region of the atherectomy device of FIG. 1;

FIG. 3 is a further detailed perspective view of the slotted tubular member of the cutting region of FIG. 2;

FIG. 4 is a detailed perspective view of the cutting region of an alternative embodiment of the atherectomy device of the present invention; and FIG. 5 is a detailed side sectional view of the cutting region of FIG. 4 taken along view line 5—5 of FIG. 4.

DETAILED DESCRIPTION OF THE INVENTION

The present invention provides an atherectomy device capable of negotiating and removing plaque from curved and tapered vessels, without suffering from the drawbacks of previously known devices. More particularly, an atherectomy device constructed in accordance with the principles of the present invention comprises two or more slotted tubular members connected by tapered flexible segments, so that the slotted tubular members may pass through, and sever occlusive material from, tortuous vessels. In addition, the flexible segments may be tapered to permit a cutting region of the atherectomy device to be advanced to remove occlusive material from tapered vessels.

Referring now to FIG. 1, a first illustrative embodiment of an atherectomy device constructed in accordance with the principles of the present invention is described. Device 10 comprises hollow guide catheter 11 having proximal end 12 and distal end 13. Flexible cutting region 14 extends from distal end 13 of catheter 11, and is coupled via flexible drive cable 15 to controller 16. Controller 16 comprises a motor and circuitry, actuated by footpedal 17, that rotates and/or longitudinally reciprocates drive cable 15 and cutting region 14, as is per se known. Controller 16 may be configured as described, for example, in U.S. Pat. No. 5,366,464 to Belknap, which is incorporated herein by reference.

Catheter 11 may include one or more ports 18 for inducing suction to aspirate severed material from the operative site, as described hereinbelow. Drive cable 15 and flexible cutting region 14 preferably include a central lumen that accepts guide wire 19, to assist in percutaneously and transluminally inserting atherectomy device 10. Drive cable 15 may comprise, for example, a helical metal wire coil. Drive cable 15 preferably is coupled to cutting region 14 at a position within guide catheter 11, proximal of distal end 13, and is capable of transmitting rotation, and optionally, reciprocating motion, to cutting region 14.

Referring now to FIGS. 2 and 3, cutting region 14 is described, and includes tubular members 20 and 21 and tip 22 interconnected by flexible segments 23, 24 and 25. Flexible segment 23 is coupled at its proximal end, for example, by welding, friction fit, or threads, to a distal end of drive cable 15, and at its distal end to tubular member 20. Flexible segment 24 couples tubular member 20 to tubular 21, and flexible segment 25 couples tubular member 21 to tip 22. Tip 22 includes aperture 26 through which guide wire 19 passes.

Each of flexible segments 23–25 comprises a tube, preferably tapered, in which windows 27 have been cut, for example, by chemical etching, or laser or electron beam cutting, to create a flexible lattice of hoops 28 interconnected by cross-members 29. Flexible segments 23–25 may be integrally formed with tubular members 20 and 21 and tip 22, or may be separately formed and joined by techniques per se known. Applicant has determined that by adjusting the wall thickness and length of the flexible segments and tubular members, the area of windows 27 and the number of cross-members 29, a flexible segment having a desired degree of strength and flexibility may be obtained. Alternatively, flexible segments 23–25 may comprise sections of helical coil or bellows-shaped tube.

Tubular members 20 and 21, and tip 22, may be separately formed and coupled by conventional techniques, e.g., welding, threads, friction fit, etc., between flexible segments 23–25, or may be integrally formed with flexible segments 23–25. Each of tubular members 20 and 21 is formed from a single-piece hollow tube by cutting slots 30 that extend for a portion of the circumference of the tubular member, and include sharpened cutting edges 31. Cutting edges 31 also may be formed to extend beyond the exterior surface of the tubular member, as shown in FIG. 3, to provide device 10 with a cutting diameter larger than that of the tubular member. Each tubular member 20 and 21 may have a uniform diameter, or may be tapered from one end to the other to match the diameters of the flexible segments to which the tubular member is coupled.

Guide catheter 11 may comprise a material typically used in catheter construction, such as polyethylene, polypropylene or urethane. Flexible segments 23–25, tubular members 20 and 21, and tip 22 preferably are formed from a high strength metal or metal alloy, such as stainless steel or nickel titanium. Alternatively, high strength plastic materials may be used for some or all of these components. Flexible segments 23–25 also may comprise metal, metal alloy or high strength plastic tapered helical coil sections.

In accordance with the principles of the present invention, the relative lengths of the tubular members and the flexible segments may be selected so that cutting region 14 is capable of bending within, and therefore removing occlusive material from, a vessel having a predetermined radius. In particular, previously known atherectomy devices such as described in the above-mentioned patents to Simpson and Clark are impracticable to use in curved vessels. The present invention, however, enables a series of relatively short tubular members, interconnected by short flexible segments, to be assembled that provides a very flexible device.

With respect to FIGS. 4 and 5, an alternative embodiment of the atherectomy device of the present invention is described. Atherectomy device 35 is constructed as described above for the embodiment of FIG. 1. In addition, the components of the cutting region, except slots 30 and cutting edges 31, include cover 36 comprising a flexible plastic or elastomeric material, such as polyethylene, urethane, or nylon. Cover 36 also may be impregnated with or coated with a lubricious material, such as polytetrafluoroethylene, to reduce abrasion of the vessel walls in the areas not contacted by cutting edges 31.

In FIG. 5, atherectomy device 35 includes lumen 37, which may be coupled by suitable means to port 18 of guide catheter 11. Lumen 37 may comprise a tube formed of materials typically used in catheter construction, and may be used to aspirate severed material from the operative site, to inject contrast agents, dyes, fluids (e.g., saline), or drugs to the operative site, or combinations thereof.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. An atherectomy device comprising:
   a drive cable;
   a tip;
   first and second tubular members, each one of the first and second tubular members integrally formed from a single-piece tube and having a portion defining a slot and a cutting edge disposed along the slot; and
   a plurality of flexible segments, a first one of the plurality of flexible segments coupled between the first tubular member and the drive cable, a second one of the plurality of flexible segments coupled between the first and second tubular members, and a third one of the plurality of flexible segments coupled between the second tubular member and the tip.

2. The atherectomy device of claim 1 wherein the first and second tubular members and plurality of flexible segments are integrally formed from a single-piece hollow tube.

3. The atherectomy device of claim 1 wherein each one of the plurality of flexible segments is tapered in a longitudinal direction.

4. The atherectomy device of claim 1 wherein the first and second tubular members are tapered in a longitudinal direction.

5. The atherectomy device of claim 1 further comprising a cover disposed on the plurality of flexible segments.

6. The atherectomy device of claim 5 wherein the cover further comprises a lubricious material.

7. The atherectomy device of claim 1 wherein each one of the plurality of flexible segments further comprises at least two hoop portions interconnected by cross-members.

8. The atherectomy device of claim 1 further comprising a guide catheter having a lumen and a distal end, wherein the drive cable is disposed in the lumen and the first flexible segment extends beyond the distal end.

9. The atherectomy device of claim 1 further comprising a lumen configured for aspirating occlusive material severed by the cutting edges of the first and second tubular members.

10. The atherectomy device of claim 1 further comprising a lumen configured for injecting a contrast agent, dye, fluid or drug.

11. The atherectomy device of claim 1 wherein the first tubular member has an exterior diameter and the cutting edge of the first tubular member extends beyond the exterior diameter.

12. The atherectomy device of claim 1 wherein the cable is configured to transmit rotational motion to the first one of the plurality of flexible segments.

13. The atherectomy device of claim 1 wherein the cable is configured to transmit reciprocatory motion to the first one of the plurality of flexible segments.

14. An atherectomy device comprising:
a drive cable;
a first tubular member integrally formed from a first portion of hollow tube and having a portion defining a first slot and a first cutting edge disposed along the first slot;
a first flexible segment connecting the first tubular member to the drive cable;
a second tubular member integrally formed from a second portion of hollow tube and having a portion defining a second slot and a second cutting edge disposed along the second slot; and
a second flexible segment connecting the first and second tubular members.

15. The atherectomy device of claim 14 wherein the first and second portions of hollow tube comprise first and second portions of a single-piece hollow tube, the first and second tubular members and first and second flexible segments are integrally formed from the single-piece hollow tube.

16. The atherectomy device of claim 14 wherein each one of the plurality of flexible segments is tapered in a longitudinal direction.

17. The atherectomy device of claim 14 wherein the first and second tubular members are tapered in a longitudinal direction.

18. The atherectomy device of claim 14 further comprising a cover disposed on the first and second flexible segments.

19. The atherectomy device of claim 18 wherein the cover further comprises a lubricious material.

20. The atherectomy device of claim 14 wherein each one of the first and second flexible segments further comprises at least two hoop portions interconnected by cross-members.

21. The atherectomy device of claim 14 further comprising a guide catheter having a lumen and a distal end, wherein the drive cable is disposed in the lumen and the first flexible segment extends beyond the distal end.

22. The atherectomy device of claim 14 further comprising a lumen configured for aspirating occlusive material severed by the cutting edges of the first and second tubular members.

23. The atherectomy device of claim 14 further comprising a lumen configured for injecting a contrast agent, dye, fluid or drug.

24. The atherectomy device of claim 14 wherein the first tubular member has an exterior diameter and the cutting edge of the first tubular member extends beyond the exterior diameter.

25. The atherectomy device of claim 14 wherein the cable is configured to transmit rotational motion to the first flexible segment.

26. The atherectomy device of claim 14 wherein the cable is configured to transmit reciprocatory motion to the first flexible segment.

* * * * *